US007077855B2

(12) United States Patent
Curtis

(10) Patent No.: US 7,077,855 B2
(45) Date of Patent: Jul. 18, 2006

(54) PRESSURE CLAMP FOR RELIEVING A HEADACHE

(76) Inventor: Patrick M. Curtis, 2141 Salem Ave., North, St. Petersburg, FL (US) 33714

( * ) Notice: Subject to any disclaimer, the term of this patent is extended or adjusted under 35 U.S.C. 154(b) by 140 days.

(21) Appl. No.: 10/439,790

(22) Filed: May 15, 2003

(65) Prior Publication Data

US 2003/0195558 A1 Oct. 16, 2003

Related U.S. Application Data

(62) Division of application No. 09/694,454, filed on Oct. 23, 2000, now abandoned, which is a division of application No. 09/344,019, filed on Jun. 25, 1999, now abandoned.

(51) Int. Cl.
*A61B 17/28* (2006.01)
*A61B 17/04* (2006.01)

(52) U.S. Cl. ...................... 606/204; 606/151; 606/157; 606/158

(58) Field of Classification Search ................ 606/151, 606/157–158, 204
See application file for complete search history.

(56) References Cited

U.S. PATENT DOCUMENTS 459,845 A 9/1891 Thomas
461,069 A 10/1891 Caspar
557,452 A 3/1896 Thompson et al.
580,954 A 4/1897 Ray
672,881 A 4/1901 Allen
682,785 A 9/1901 Caldwell
794,561 A 7/1905 Spencer
807,706 A 12/1905 Allen
908,256 A 12/1908 Harrison
1,025,280 A 5/1912 Lawlor
1,310,551 A 7/1919 Solberg
1,453,863 A 5/1923 Conard
1,782,752 A 11/1930 Weisler
2,005,090 A 6/1935 Kreiger
2,325,868 A 8/1943 Morrow
2,620,800 A 12/1952 Powers
2,748,470 A 6/1956 Borden
2,849,777 A 9/1958 Ridgers et al.
2,964,869 A 12/1960 Berghoff et al.
3,203,421 A * 8/1965 Bialick ........................ 128/885
3,736,629 A 6/1973 Blake
3,909,889 A 10/1975 Emerson
4,227,302 A 10/1980 Torrance
4,549,536 A * 10/1985 Varjabedian ................ 601/135
4,617,736 A 10/1986 McCrary
4,619,447 A 10/1986 Blake
5,021,058 A 6/1991 McKee
5,094,227 A * 3/1992 Eglauf et al. ............... 601/135
5,302,039 A 4/1994 Omholt
5,423,853 A 6/1995 Lasvignes
5,571,125 A 11/1996 Chadwick
5,584,854 A 12/1996 Minarik

FOREIGN PATENT DOCUMENTS

EP 0135202 * 3/1985

* cited by examiner

*Primary Examiner*—Gary Jackson
(74) *Attorney, Agent, or Firm*—Larson & Larson, PA; Herbert W. Larson

(57) ABSTRACT

A clamp is positioned in a fleshy area of a person's hand between the thumb and index figure. The clamp has a top and bottom arm with a thumb screw to close a gap between the arms over the fleshy area of a person's hand and is left in place for two to three minutes or until the person's headache is relieved. Thereafter, the clamp is removed and stored for future use.

4 Claims, 4 Drawing Sheets

PRESSURE CLAMP FOR RELIEVING A HEADACHE

PRIOR APPLICATIONS

This application is a continuation-in-part from application Ser. No. 09/344,019, filed Jun. 25, 1999 now abandoned. and a divisional of application Ser. No. 09/694,454, filed Oct. 23, 2000 now abadoned.

BACKGROUND OF THE INVENTION

1. Field of The Invention

This invention relates to a device for relieving headaches. More particularly, it relates to a device and method for relieving a headache wherein there is provided a device for clamping to the hand of a person experiencing a headache to effect a reduction of tension.

2. Description of Prior Art

Clamping devices are well known in the prior art. Numerous designs of clamps have been used for years everywhere from carpentry to manufacturing to medical uses. For instance, clamps are used extensively by carpenters when gluing two structures together; in manufacturing environments by tool and die makers; and by doctors in surgical procedures (i.e., to "clamp-off" arteries).

As to medical clamps, the applicant is aware of many devices used for specific purposes. U.S. Pat. No. 580,954 to Ray discloses a clamping device for correcting nasal deformity. U.S. Pat. No. 2,620,800 to Powers discloses a hemorrhoidal clamp for clamping a portion of rectum tissue between a head and seat of the device. U.S. Pat. No. 5,571,125 to Chadwick discloses a device for clamping the penis of incontinent males to prohibit the unwanted flow of urine. All of the aforementioned devices work on a basic principle of the clamp wherein pressure is applied between two members. However, none of these references nor any other references known to the applicant disclose, teach or suggest a method of relieving a headache wherein a novel clamp is applied to a point on the human hand.

Headaches are a common problem experienced by most humans at some point in their lives. Some types of headaches are so severe that they are known to incapacitate people (i.e., caused by nasal congestion and the common cold), while still others are self-inflicted (i.e., alcohol intoxication). Regardless of the cause, most people agree that it is difficult to function. Many people find that they cannot concentrate on their work while others even find it difficult to operate their vehicles. It is therefore extremely common for people to seek out a "cure" for their headache.

The most common means today of "curing" a headache is to take an over-the-counter pain medication. Numerous medications are available and include aspirin, ibuprofen, and acetaminophen. Unfortunately, the use of such medications, especially over long periods of use, can lead to "side-effect" complications. Aspirin is known to thin the blood and can be dangerous to those who have low platelet blood counts. Ibuprofen is known to be damaging to the liver over long periods of use. Additionally, almost all pain medications should not be combined with the use of alcohol. This is a big problem since many people take the aforementioned pain medications after a heavy night of alcohol consumption. Accordingly, a means to relieve a headache is needed which does not jeopardize the health of humans due to side-effects and dangers of combinations with other drugs and stimulants. Such treatment should be easy for the person experiencing the headache to administer (i.e., not require special training), as well as be inexpensive.

SUMMARY OF THE INVENTION

I have invented a device which can be employed with a method to relieve a human headache. Such method does not require special medical training, does not include the administration of drugs, and does not result in any side-effects from one-time or prolonged use. The device used is small, unobtrusive and inexpensive to manufacture and, therefore, inexpensive for the consumer.

A clamp having an upper and lower arm extending outwardly from a pivot point is placed between a person's index finger and thumb. A thumb screw on the clamp is tightened and left on the hand for about fifteen to thirty minutes. The clamp is then removed and it is expected that a stress headache will have disappeared.

These and other aspects and features of the invention will be better understood from the following detailed description of the preferred embodiment when read in conjunction with the appended drawing figures.

SPECIFIC DESCRIPTION OF THE PREFERRED EMBODIMENT

Figure 1:
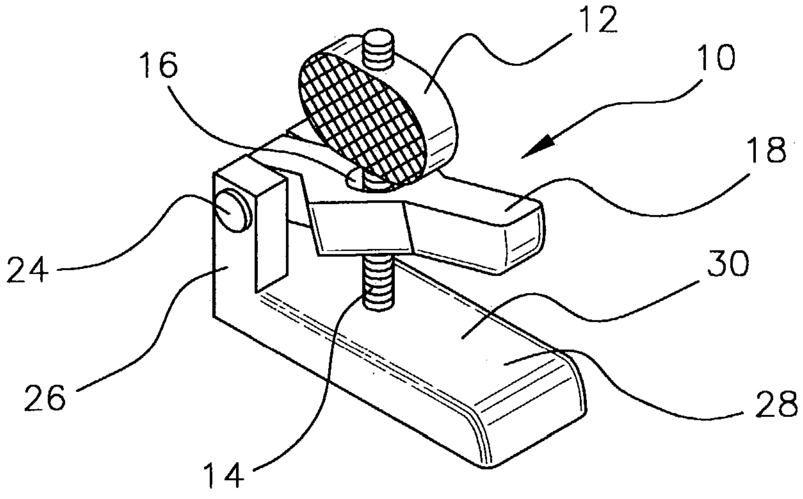
FIG. 1 is a perspective view of a clamp used in the method of this invention.
Figure 2:
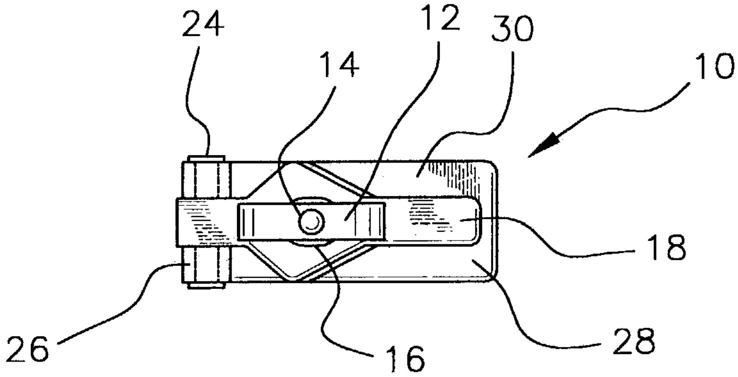
FIG. 2 is a top plan view of the clamp of FIG. 1.
Figure 3:
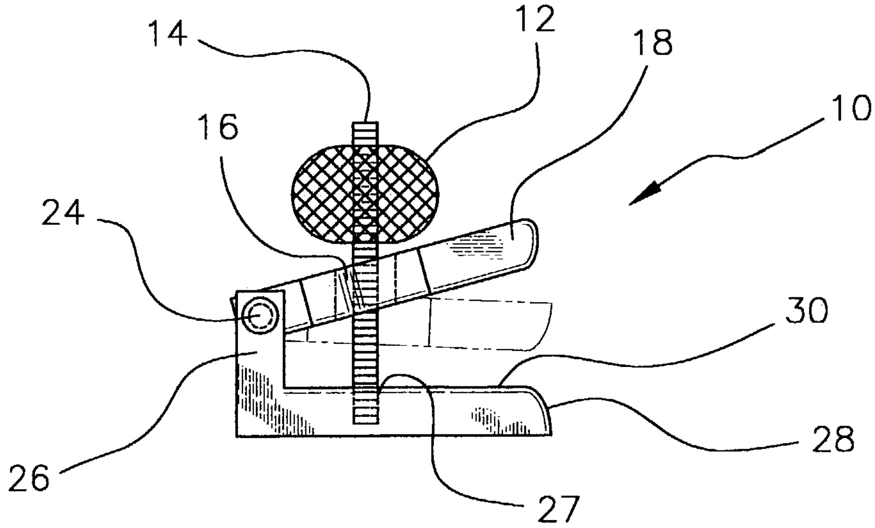
FIG. 3 is a side elevational view of the clamp of FIG. 1

Reference is first made to FIGS. 1–3 wherein a pressure clamp 10 used in the method of this invention is depicted. The clamp 10 has a screw handle 12 containing a threaded screw 14 which upon being turned through bore 16 in pivoting upper arm 18 presses downwardly toward a top surface (treatment site) 20 of a person's hand 22.

Arm 18 pivots at a bolt 24 contained in an upright portion 26 of an L-shaped base arm 28. A depression 27 in top surface 30 of base arm 28 acts as a stop for the screw 14 to prevent over tightening.

Figure 4:
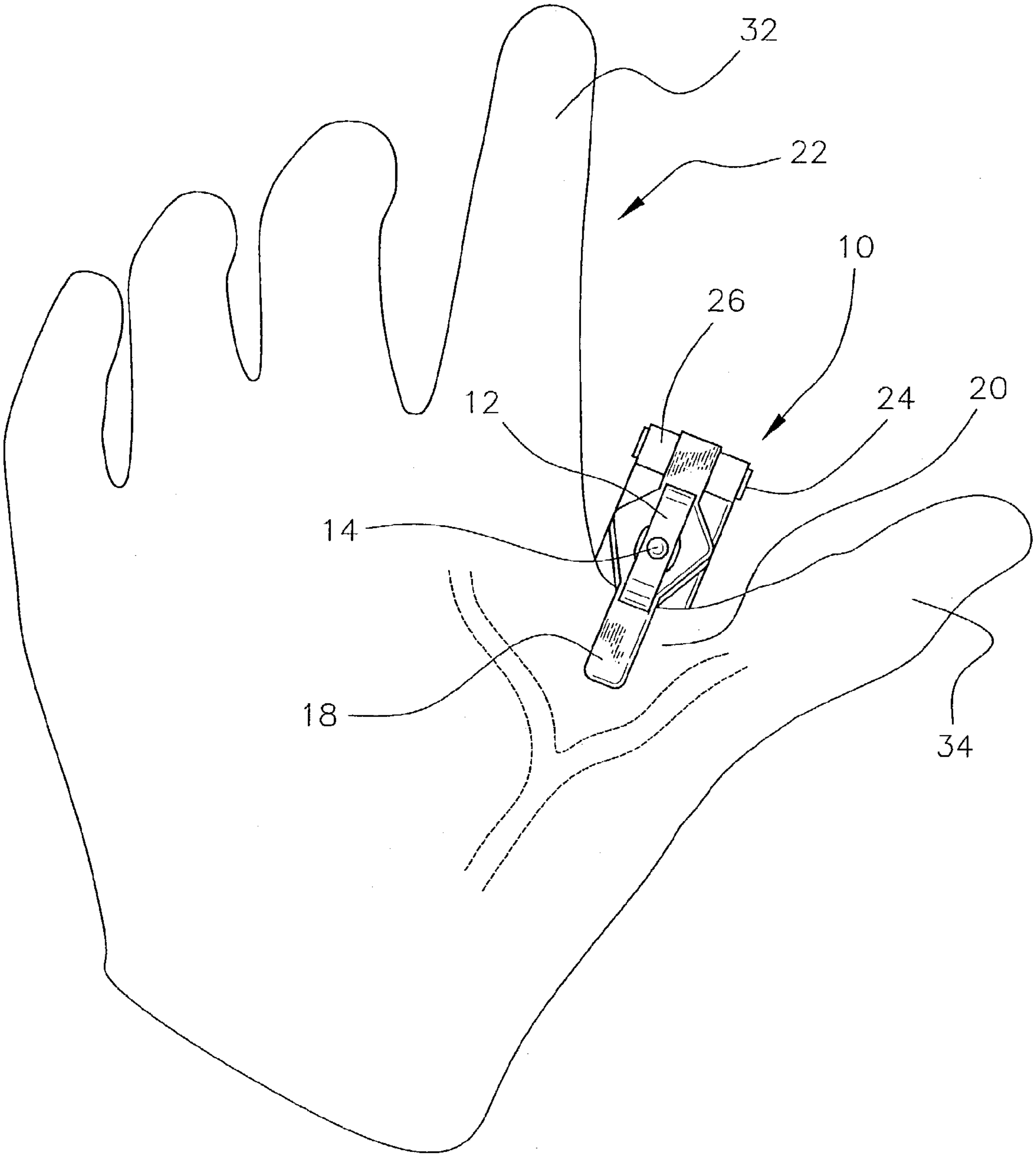
FIG. 4 shows the clamp of FIG. 1 positioned on the hand of a patient.

FIG. 4 shows the clamp 10 screwed in place between the index finger 32 and the thumb 34 of a person so that pressure is placed on top surface 20 of the person's hand.

Figure 6:
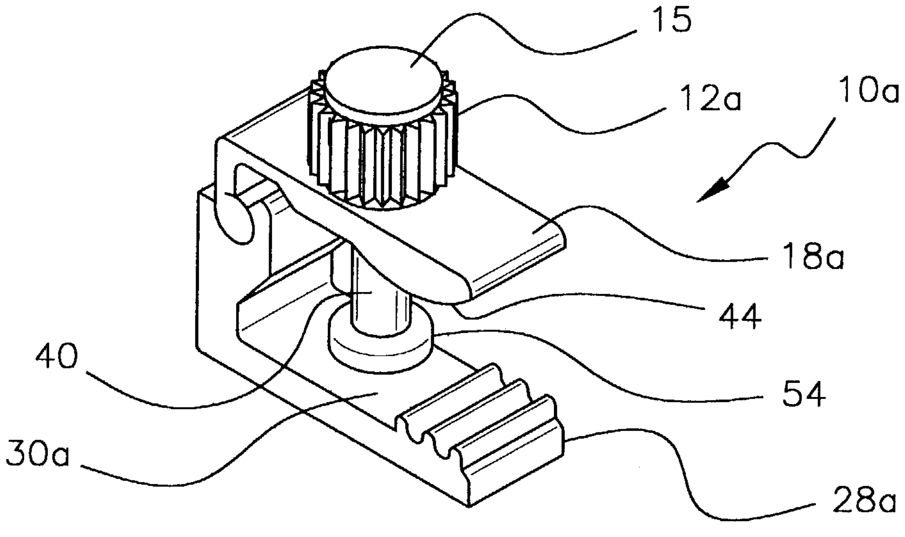
FIG. 6 is a perspective view of an alternative clamp used in the method of this invention.
Figure 7:
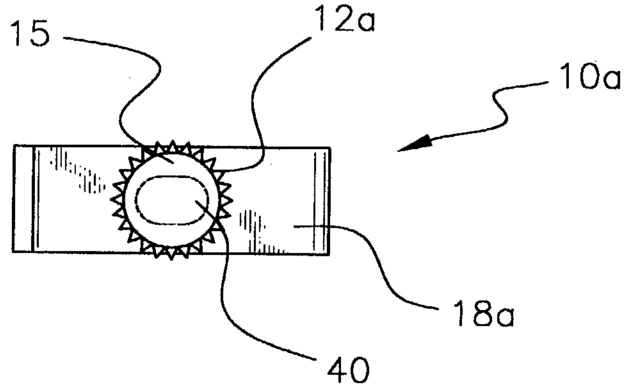
FIG. 7 is a top plan view of the clamp of FIG. 6.
Figure 8:
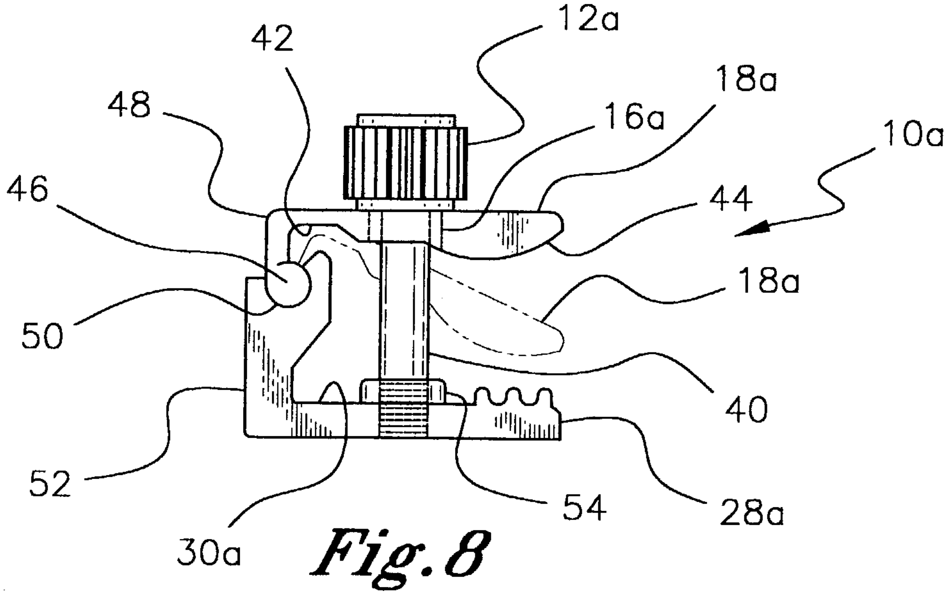
FIG. 8 is a side elevational view of the clamp of FIG. 6.

Referring to FIGS. 6–8 an alternate clamp for use in the method of this invention is depicted. The clamp 10*a* has a finger grip 12*a* attached to cylindrical member 15 which is in turn attached to a shaft 40 which passes downwardly through a bore 16*a* in an upper arm 18*a*. A bottom surface 42 of upper arm 18*a* has a convex portion 44 at an end portion distal from a pivot ball 46. Convex portion 44 is the portion of the clamp 10*a* which engages the top surface 20 of a person's hand 22. A back portion 48 of the upper arm 18*a* is L-shaped and descends to the pivot ball 46 which engages a receiving socket 50 in an upper back portion 52 of lower arm 28*a*. Arm 28*a* is also L-shaped and has an upper surface 30*a* on which is positioned a collar 54 containing inner threads (not shown) which engage threads (not shown) at a bottom portion of shaft 40.

Figure 5:
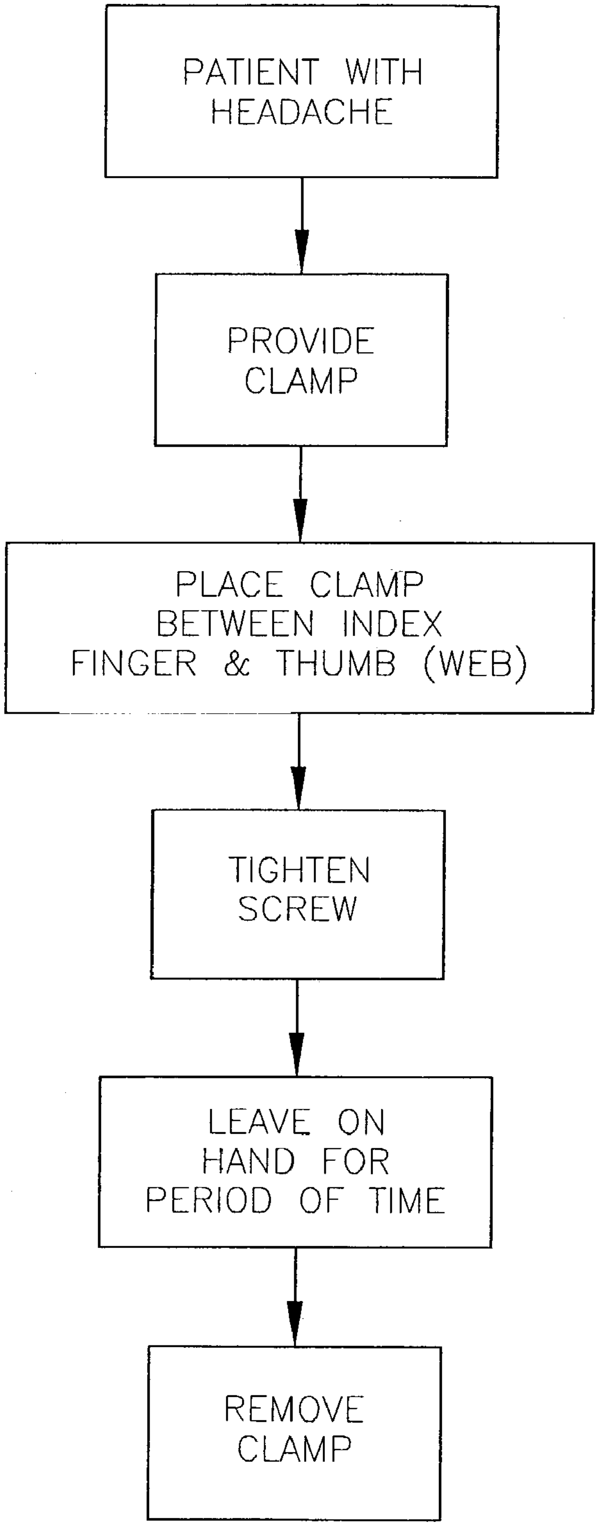
FIG. 5 is a diagrammatic description of the method steps employed in this invention.

FIG. 5 describes the steps employed in the method of this invention to treat a headache. The clamp 10 or 10*a* shown in FIGS. 1–3 and 6–8 is placed between the index finger 32 and thumb 34 of a person over a fleshy hand surface 20. The top pivoting arm 18 or 18*a*, bottom convex surface 44 and the base top surface 30 or 30*a* place pressure on a hand treatment site 20 as the screw handle 12 or 12*a* is turned clockwise. When a comfort level is reached the screw handle 12 or 12*a* is not turned further. The depression 27 in top surface 30 of the clamp 10 acts as a stop and ensures that the clamp will not be too tightly placed over surface 20. The collar 54 on clamp 10*a* contains inner threads that engage threads on the bottom of shaft 40 as arm 18*a* is depressed. Usually the clamp is left on surface 20 for two to three minutes or for as long as it takes for the headache to subside. Thereafter, the screw handle is turned counter-clockwise and the clamp is removed from the person's hand 22.

The clamp top arm 18 or 18*a* and bottom arm 28 or 28*a* can be made from a high strength plastic such as polyethylene, polypropylene, or a copolymer. The screw 14 is made of a metal and alternatively the entire clamp can be made of a metal such as aluminum or stainless steel. Shaft 40 on clamp 10*a* can be made of a metal or high strength plastic.

Of course various changes, modifications and alterations in the teachings of the present invention may be contemplated by those skilled in the art without departing from the intended spirit and scope thereof.

As such it is intended that the present invention only be limited by the terms of the appended claims and equivalent elements.

I claim:

1. A medical device configured for exerting pressure on a person's fleshy part of his or her hand between the thumb and index finger for relieving a headache, the medical device comprising:

an upper arm and a lower arm pivoting together at a first end of each arm at a point distal from the fleshy part of the hand;

a thumb screw turning a shaft passing through a bore in the upper arm to threadably engage threads in the lower arm so that turning the thumb screw causes the upper arm to move downwardly to close a gap between a second end of the upper and lower arms with the fleshy part of the hand squeezed between the first and second ends;

the upper arm having a downwardly descending leg at the first end, the leg terminating in a ball engaging a socket in an upwardly ascending leg at the first end of the lower arm; and a bottom surface of the upper arm second end having a convex surface and together with a top surface of the lower arm second end adapted to engage the fleshy part of the hand in a tight configuration when the thumb screw has depressed the upper arm.

2. A medical device according to claim 1 wherein a top surface of the bottom arm at a portion proximal to the fleshy part of the hand has multiple ridges to prevent slippage of the medical device.

3. The medical device according to claim 1 wherein the medical device components are made from a high strength plastic.

4. The medical device according to claim 1 wherein the medical device components are made from a metal.

* * * * *